United States Patent [19]

Andrews et al.

[11] Patent Number: 4,630,897
[45] Date of Patent: Dec. 23, 1986

[54] LIQUID CRYSTAL COMPOUNDS

[75] Inventors: Beatrice M. Andrews, Grimsby; Neil Carr, Hull, both of United Kingdom; George W. Gray, Cottingham; Christine Hogg, Beverley, both of England

[73] Assignee: The Secretary of State for Defence in Her Britannic Majesty's Government of the United Kingdom of Great Britain and Northern Ireland, London, England

[21] Appl. No.: 697,624

[22] Filed: Feb. 4, 1985

Related U.S. Application Data

[62] Division of Ser. No. 501,783, Jun. 7, 1983, Pat. No. 4,512,636.

[30] Foreign Application Priority Data

Jun. 15, 1982 [GB] United Kingdom ............... 8217355

[51] Int. Cl.$^4$ .................... C09K 3/34; G02F 1/13; C07D 319/06
[52] U.S. Cl. .................... 350/350 R; 252/299.5; 252/299.61; 549/369; 549/373; 549/374
[58] Field of Search ............... 549/373, 372, 369, 374; 252/299.61, 299.63, 299.5; 350/350 R, 350 S

[56] References Cited

U.S. PATENT DOCUMENTS

| | | | |
|---|---|---|---|
| 4,062,798 | 4/1981 | Boller et al. | |
| 4,261,651 | 4/1981 | Gray et al. | 252/299.63 |
| 4,298,528 | 11/1981 | Sethofer | 252/299.61 |
| 4,322,354 | 3/1982 | Sorkin | 252/299.61 |
| 4,325,830 | 4/1982 | Sethofer | 252/299.61 |
| 4,344,856 | 8/1982 | Demus et al. | 252/299.61 |
| 4,348,324 | 9/1982 | Demus et al. | 252/299.61 |
| 4,398,803 | 8/1983 | Pohl et al. | 252/299.01 |
| 4,415,470 | 11/1983 | Eidenschink et al. | 252/299.63 |
| 4,419,264 | 12/1983 | Eidenschink et al. | 252/299.63 |
| 4,439,015 | 3/1984 | Rich et al. | 252/299.63 |
| 4,455,443 | 6/1984 | Takatsu et al. | 252/299.63 |
| 4,482,472 | 11/1984 | Carr et al. | 252/299.5 |

FOREIGN PATENT DOCUMENTS

| | | | |
|---|---|---|---|
| 56501 | 7/1982 | European Pat. Off. | 252/299.61 |
| 58512 | 8/1982 | European Pat. Off. | 252/299.62 |
| 58981 | 9/1982 | European Pat. Off. | 252/299.5 |
| 72204 | 2/1983 | European Pat. Off. | 252/299.62 |
| 84194 | 7/1983 | European Pat. Off. | 252/299.61 |
| 3233641 | 3/1983 | Fed. Rep. of Germany | 252/299.63 |
| 2067188 | 7/1981 | United Kingdom | 252/299.61 |
| 2086385 | 5/1982 | United Kingdom | 252/299.63 |

Primary Examiner—Teddy S. Gron
Attorney, Agent, or Firm—Nixon & Vanderhye

[57] ABSTRACT

A novel liquid crystal compound has a formula:

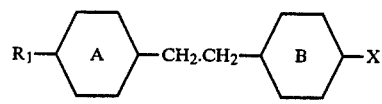

where:

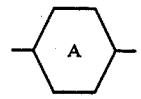

is a trans-2,5-disubstituted-1,3-dioxan ring or a 2,5-disubstituted-1,3-pyrimidine ring

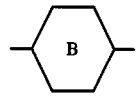

is a 1,4-disubstituted benzene ring optionally containing one or more F, Cl or $CH_3$ groups as lateral substituents; $R_1$ is an alkyl group; and X is a terminal group selected from H, CN, Cl, F and $R_2$ where $R_2$ is selected from alkyl $R_3$, alkoxy $OR_3$, alkylcarbonyloxy $OCOR_3$ and alkoxycarbonyloxy $OCOOR_3$.

4 Claims, 7 Drawing Figures

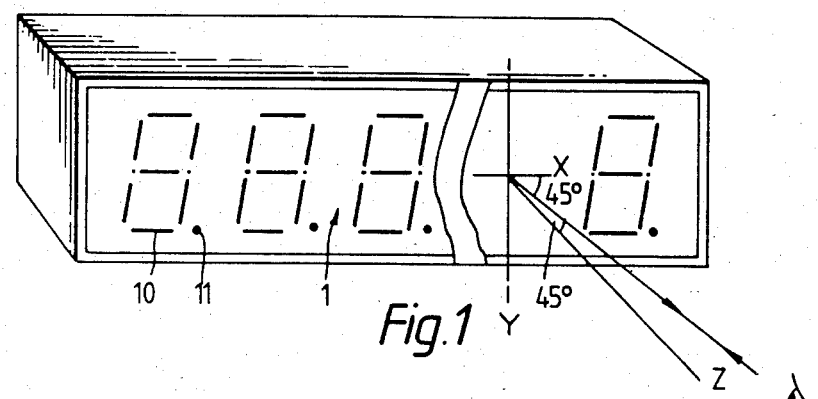
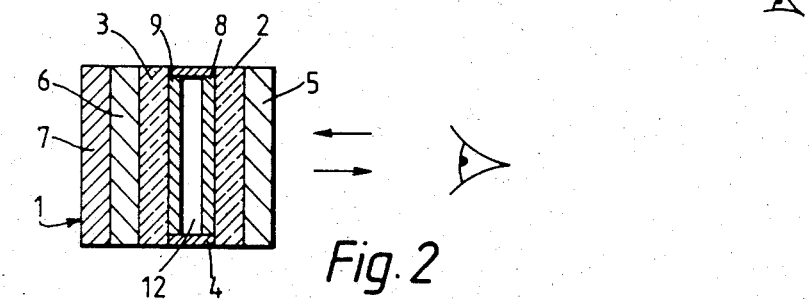
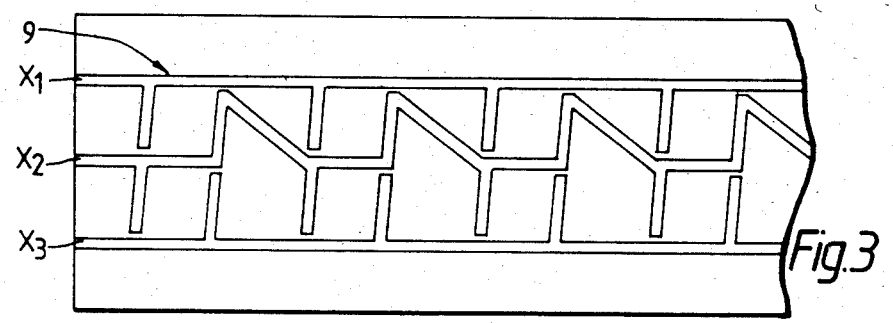
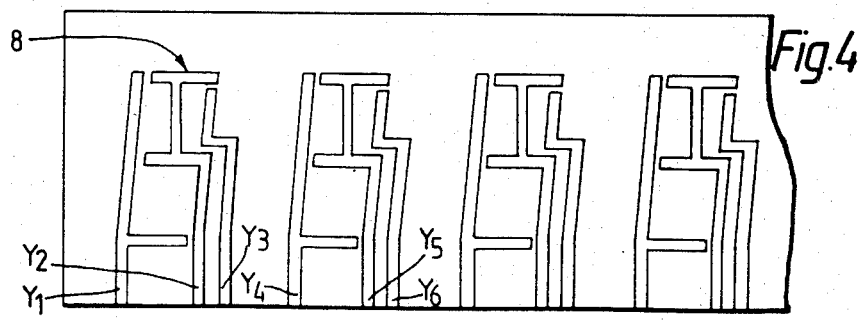

LIQUID CRYSTAL COMPOUNDS

This is a division of application Ser. No. 501,783 filed June 7, 1983 allowed Nov. 29, 1984, now U.S. Pat. No. 4,512,636.

The present invention relates to liquid crystal materials.

The use of liquid crystal materials to exhibit electro-optical effects in display devices such as digital calculators, watches, meters and simple word displays is now well known. However known liquid crystal materials are not ideal in all respects and a considerable amount of work is currently being carried out in the art to improve their properties. Liquid crystal materials normally consist of mixtures of compounds and improved materials are obtained by forming new mixtures having an improved combination of properties.

The purpose of the present invention is to provide a novel family of liquid crystal compounds which may be used in mixtures, particularly wide temperature range nematic liquid crystal mixtures, to provide in certain cases improved properties.

According to the present invention there is provided a liquid crystal compound having a formula:

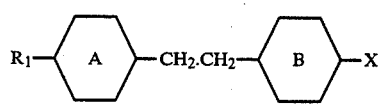

Formula I where:

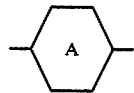

is a trans-2,5-disubstituted-1,3-dioxan ring or a 2,5-disubstituted-1,3-pyrimidine ring

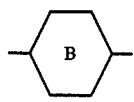

is a 1,4-disubstituted benzene ring optionally containing one or more F, Cl or $CH_3$ groups as lateral substituents; $R_1$ is an alkyl group; and X is a terminal group selected from H, CN, Cl, F and $R_2$ where $R_2$ is selected from alkyl $R_3$, alkoxy $OR_3$, alkylcarbonyloxy $OCOR_3$ and alkoxycarbonyloxy $OCOOR_3$.

Preferably, if

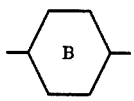

is laterally substituted it is

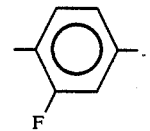

Examples of compounds of Formula I are those of Formulae Ia to Ih as follows:

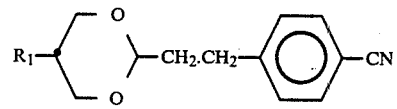

Formula Ia

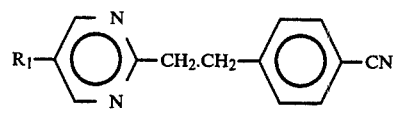

Formula Ib

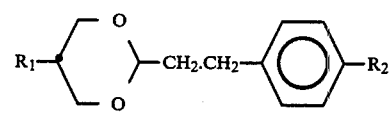

Formula Ic

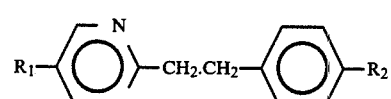

Formula Id

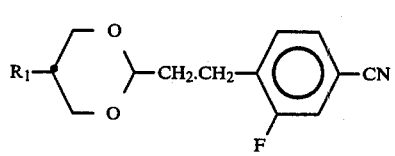

Formula Ie

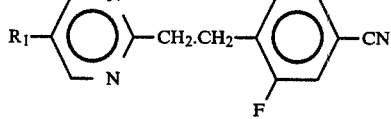

Formula If

Formula Ig

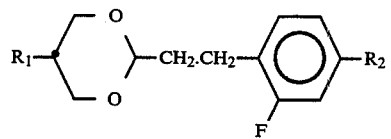

Formula Ih

Preferably, $R_1$ and $R_3$ are independently alkyl groups having from 1 to 18, desirably 1–9 carbon atoms. These groups may be n-alkyl or branched alkyl groups. If branched, they may contain a chiral centre.

Generally speaking the compounds of Formula I are liquid crystal compounds having a relatively low melting point (usually less than 100° C.). They show a range of Δε (dielectric anisotropy at low frequencies) values depending on group X. Where X is CN Δε is generally greater than 10 and positive. Where X is F or Cl Δε is generally greater than 3 but less than 10. Where X is H or $R_2 \Delta\epsilon$ is generally less than 3 and may be positive or negative. $\Delta\epsilon$ is generally negative where X is H or $R_2$ and

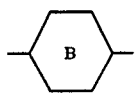

is laterally substituted.

The compounds of Formula I may show improved properties compared with known ethyl bridged liquid crystal compounds.

For example, the compounds of Formula Ia and Ib can show a higher positive dielectric anisotropy $\Delta\epsilon$ than the known cyclohexane compounds of Formula

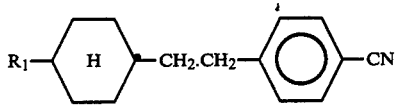

This allows lower operation (threshold) voltages to be used when the compounds of Formula I are contained in liquid crystal materials which are used in electro-optical displays.

It is believed that higher dielectric anisotropy is possible due in part to a greater steric hindrance of dipole-dipole pairing this providing a greater number of dipoles which contribute to the permittivity (along the average molecular axis); also it is believed that the longitudinal dipole 11 along the average molecular axis is greater.

The compounds of formula $I_c$, $I_d$, $I_g$ and $I_h$ can also be of value in widening the range of low or moderate viscosity additives for improving the multiplexibility of mixtures of cyano-substituted materials. They also offer lower

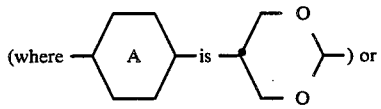

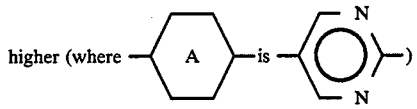

refractive indices than known compounds containing cyclohexane or benzene rings in place of ring

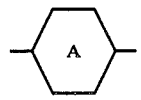

thus providing a greater versatility of optical properties and they also show a more negative $\Delta\epsilon$ value in the case of certain laterally substituted compounds eg of Formula 1g and 1h.

The compounds of Formula I can also reduce the tendency to form smectic phases in mixtures in which they are incorporated.

By a 'liquid crystal compound' is meant a compound in one of the following two known categories:

(i) compounds which normally exhibit a liquid crystal phase;
(ii) compounds which do not normally exhibit a liquid crystal phase but which nevertheless usefully affect some aspect of liquid crystal behaviour when dissolved in other liquid crystal compounds.

Compounds in category (ii) show a 'monotropic' or a 'virtual' liquid crystal to isotropic liquid transition at a temperature below the melting point of their solid phase. The monotropic or virtual transition may be detected respectively by rapid cooling of the liquid phase or by dissolving the compound in a material exhibiting a liquid crystal phase, observing the change in the transition to the isotropic phase of the material by the addition and calculating the virtual transition temperature by extrapolation.

Compounds in category (ii) might for example be usefully dissolved in other liquid crystal compounds to extend or vary the liquid crystal temperature ranges of the compounds or to vary the molecular helical pitch (in the case of cholesteric liquid crystals).

One or more of compounds according to Formula I may be used in any of the following applications (where material having a positive dielectric anisotropy is referred to as 'positive' material and material having a negative dielectric anisotropy is referred to as 'negative' material);

(i) as one or more components of a positive nematic material for use in twisted nematic effect devices including multiplexed devices; an example of such a device is given below;
(ii) as one or more components of a negative material preferably also with a pleochroic dye, for use in Fréedericksz effect devices (negative nematic type) in which the molecular arrangement may be changed from the homeotropic texture (OFF state) to the homogeneous texture (ON state) by an electric field; an example of such a device is given below;
(iii) as one or more components of a positive nematic material, preferably also with a pleochroic dye, for use in Fréedericksz effect devices (positive nematic type) in which the molecular arrangement may be changed from the homogeneous texture (OFF state) to the homeotropic texture (ON state) by an electric field;
(iv) as one or more components of a negative material which is a cholesteric (chiral nematic) of suitable resistivity (about $10^9$ ohm.cm), for use in cholesteric memory mode devices in which the molecular arrangement may be changed from a homogeneous texture (OFF state) to a turbulent scattering focal conic texture (ON state) by an electric field;
(v) as one or more components of a strongly negative material which is a cholesteric, preferably together also with a pleochroic dye, for use in cholesteric-to-nematic phase change effect devices (positive contrast type) in which the molecular arrangement may be changed from a weakly scattering, ie clear, surface aligned homeotropic texture (OFF state) to a strongly scattering twisted homogeneous texture (ON state) by an electric field;
(vi) as one or more components of a positive material which is a long helical molecular pitch (eg $\sim 3$ μm) cholesteric, preferably together also with a pleochroic dye, in cholesteric-to-nematic phase change effect devices (negative contrast type) in which the molecular arrangement may be changed from a scattering focal conic texture (OFF state) to a clear homeotropic texture (ON state) by an electric field;

(vii) as one or more components of a negative nematic material of suitable resistivity (about $10^9$ ohm.cm), in dynamic scattering effect devices in which the molecular arrangement may be changed from a clear homeotropic texture (OFF state) to a turbulent scattering texture (ON state) by an electric field;

(viii) as one or more components of a positive nematic material in two frequency switching effect devices (which may be twisted nematic effect devices) in which the dielectric anisotropy of the material may be changed from (at low frequency) positive (OFF state) to negative (ON state) by the application of a high frequency electric field.

The construction and operation of the above devices and the general kinds of material which are suitable for use in them are themselves known. It will be obvious to those skilled in the art that given a particular compound of Formula I the particular applications in which the compound may be used will depend on the particular properties of the compound, especially its $\Delta\epsilon$ value.

Where a material is to be used in a twisted nematic effect, cholesteric to nematic phase change effect (negative contrast type) or Fréedericksz effect (positive nematic type) device the material may include one or more compounds of positive dielectric anisotropy selected from the following families to give a liquid crystal phase at room temperature as well as a positive dielectric anisotropy:

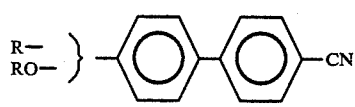

Formula (VIIa)

Formula (VIIb)

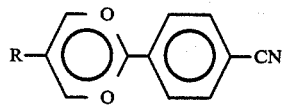

Formula (VIIc)

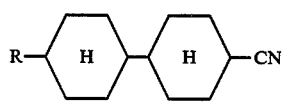

Formula (VIId)

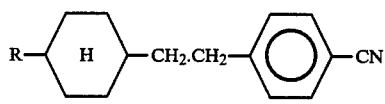

Formula (VIIe)

(preferably n-alkyl having one to seven carbon atoms). where the various groups R are the same or different alkyl groups. Typically, all positive dielectric anisotropy compounds together give between 40 to 100% by weight of the material.

The material may also contain one or more high clearing point compounds (typically up to about 25% by weight) eg selected from the following classes, to extend the liquid crystal temperature range of the material at its upper end:

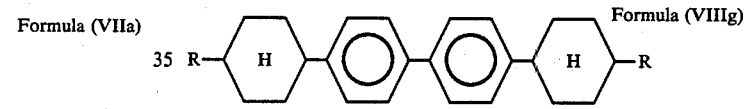

Formula (VIIIa)

Formula (VIIIb)

Formula (VIIIc)

Formula (VIIId)

Formula (VIIIe)

Formula (VIIIf)

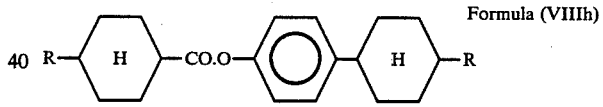

Formula (VIIIg)

Formula (VIIIh)

where each R is independently an n-alkyl group, preferably having from 1 to 7 carbon atoms.

The compounds of Formula I may be incorporated in liquid crystal materials which may be used in multiplexed twisted nematic effect devices. As taught in published UK Patent Applications 2,031,010A and 2,063,287A the multiplexibility of a strongly positive host material, together with one or more high clearing point compounds eg selected from the classes of Formulae (VIIIa to h), may be improved by the addition of a component of low dielectric anisotropy (ie weakly positive or negative). This improvement is believed to be brought about by the disruption of anti-parallel pairing of the molecules of the cyano compounds caused by introduction of the material of low dielectric anisotropy.

Depending on its dielectric anisotropy, the compound of Formula I may be incorporated in such a material either as part of the positive nematic component, eg where X in Formula I is CN or Cl, or as part of the low dielectric anisotropy component eg where X is H, or $R_2$, or both.

The component of low dielectric anisotropy may comprise one or more compounds selected from the following known families:

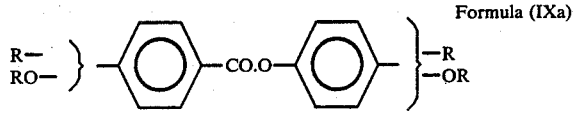
Formula (IXa)

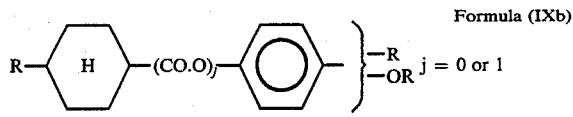
Formula (IXb) j = 0 or 1

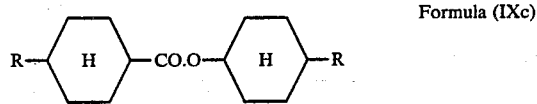
Formula (IXc)

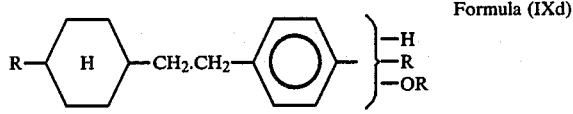
Formula (IXd)

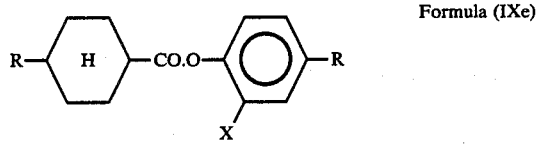
Formula (IXe)

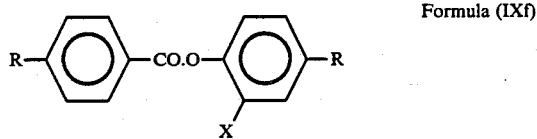
Formula (IXf)

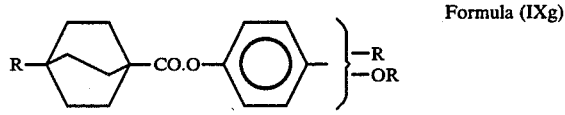
Formula (IXg)

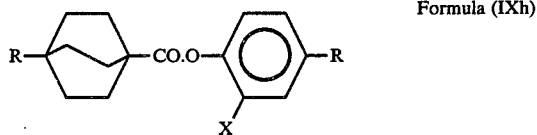
Formula (IXh)

where X=halogeno, preferably fluoro, bicyclo(2,2,-2)octane and R is as defined above.

A multiplexed twisted nematic may also contain a small amount, eg up to about 2% by weight, of a chiral additive, eg the BDH compound C 15.

Thus, a liquid crystal material suitable for a multiplexed twisted nematic effect device embodying the present invention preferably comprises the components in Table 1 as follows:

TABLE 1

Liquid crystal material composition for multiplexed twisted nematic operation.

| Component | Constituents | Percentage by weight |
|---|---|---|
| Component 1: low melting point positive compound(s) giving a room temperature nematic phase alone or mixed with other compounds. | One or more compounds selected from Formulae (VIIa) to (VIIe) above and/or one or more compounds of Formula I having Δε strongly positive. | 5-80% |
| Component 2: high clearing point liquid crystal compound(s). | One or more compounds selected from Formulae (VIIIa) to (VIIIh) above. | 5-30% |
| Component 3: low dielectric anisotropy compound(s). | One or more compounds selected from Formulae (IXa) to (IXh) and/or one or more compounds of Formula I having a small value (<2) of Δε magnitude. | 5-90% |
| Component 4: chiral compound(s) | One or more chiral compounds. | 0-2% |

The compound(s) of Formula I preferably constitutes from 5 to 80% by weight of the overall material composition.

Liquid crystal mixtures including compounds of Formula I may be formed in a known way, eg simply by heating the constituent compounds to form an overall isotropic liquid, stirring the liquid for a short period, eg about 10 minutes, and allowing it to cool.

To provide more general examples of a mixture according to the second aspect at least one compound according to Formula I above may be mixed together with one or more compounds in any one or more of the following known families for use in one or more of the applications given above (the actual application(s) depending on the mixture's properties);

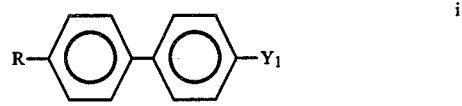
i

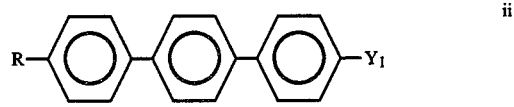
ii

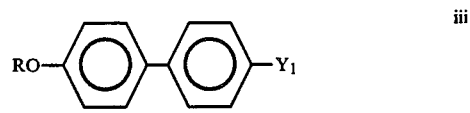
iii

iv

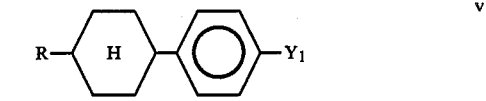
v

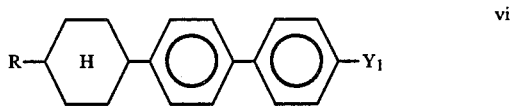
vi

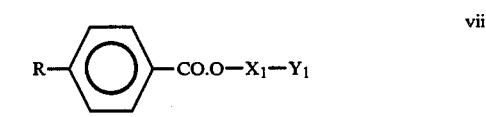
vii

-continued
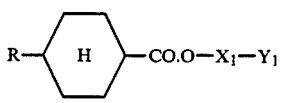
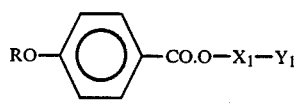
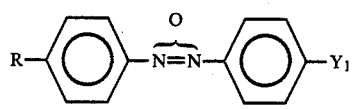
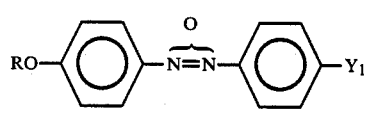
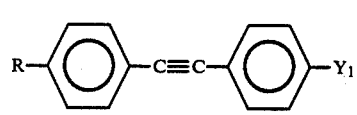
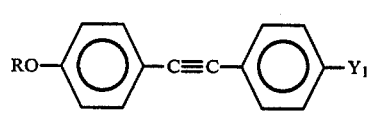
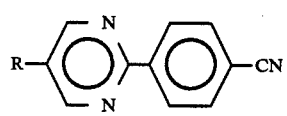
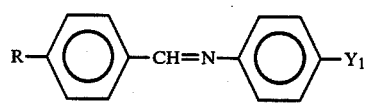
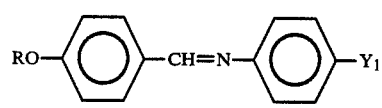
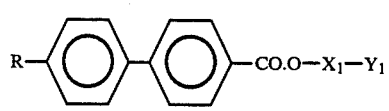
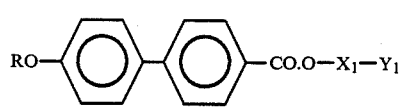
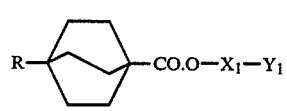
-continued
viii 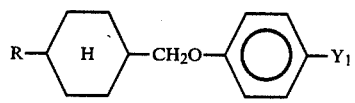
ix 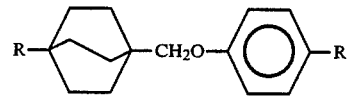
x 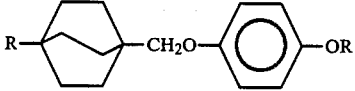
xi 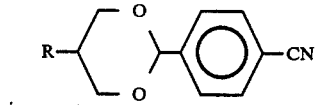
xii 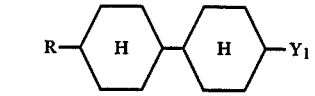
xiii 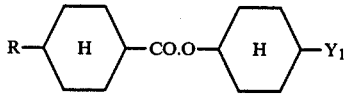
xiv 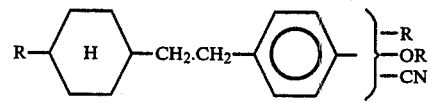
where
xv
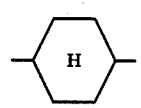
xvi
is a trans-1,4-disubstituted cyclohexane ring,
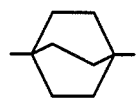
xvii
is a 1,4-disubstituted bicyclo(2,2,2)octane ring, $X_1$ is a 1,4-phenylene group
xviii
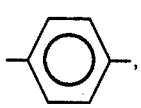
xix
a 4,4'-biphenylyl group
xx
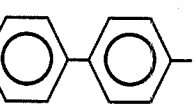
a 2,6-naphthyl group

or a trans-1,4-disubstituted cyclohexane ring, and $Y_1$ is CN, or R' or $OR^1$ or CO.O—X—$Y^1$ where $Y^1$ is CN, or R' or OR'; where R and R' are alkyl groups; or a derivative of one of these wherein H is replaced by a halogen, eg F, in one of the benzene rings.

Preferably, the compound(s) of Formula I comprises between 5 and 80% by weight of the mixture.

According to the present invention in a second aspect a liquid crystal device includes two dielectric substrates at least one of which is optically transparent, a layer of liquid crystal material sandwiched between the substrates and electrodes on the inner surfaces of the substrates to enable an electric field to be applied across the layer of liquid crystal material to provide an electro-optic effect therein, characterised in that the liquid crystal material consists of or includes a compound according to Formula I above.

The device according to the second aspect may be a twisted nematic effect device, which may or may not be operated in a multiplexed fashion, a cholesteric-to-nematic phase change effect device, a Fréedericksz effect device or a two-frequency switching effect device, all constructed in a known manner or any of the other devices mentioned above. The various ways in which compounds according to Formula I may be used in these devices are outlined above and will be further apparent to those skilled in the art.

Compounds of Formula I wherein

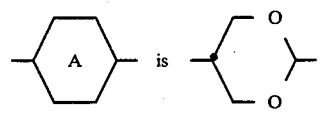

may be made by the following route, Route A:

Route A: (where $Y_1$=H, $R_3$, OH, $CO_2H$, F or Cl, and $R_1$, $R_3$ and

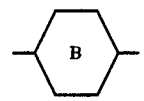

are as defined above):

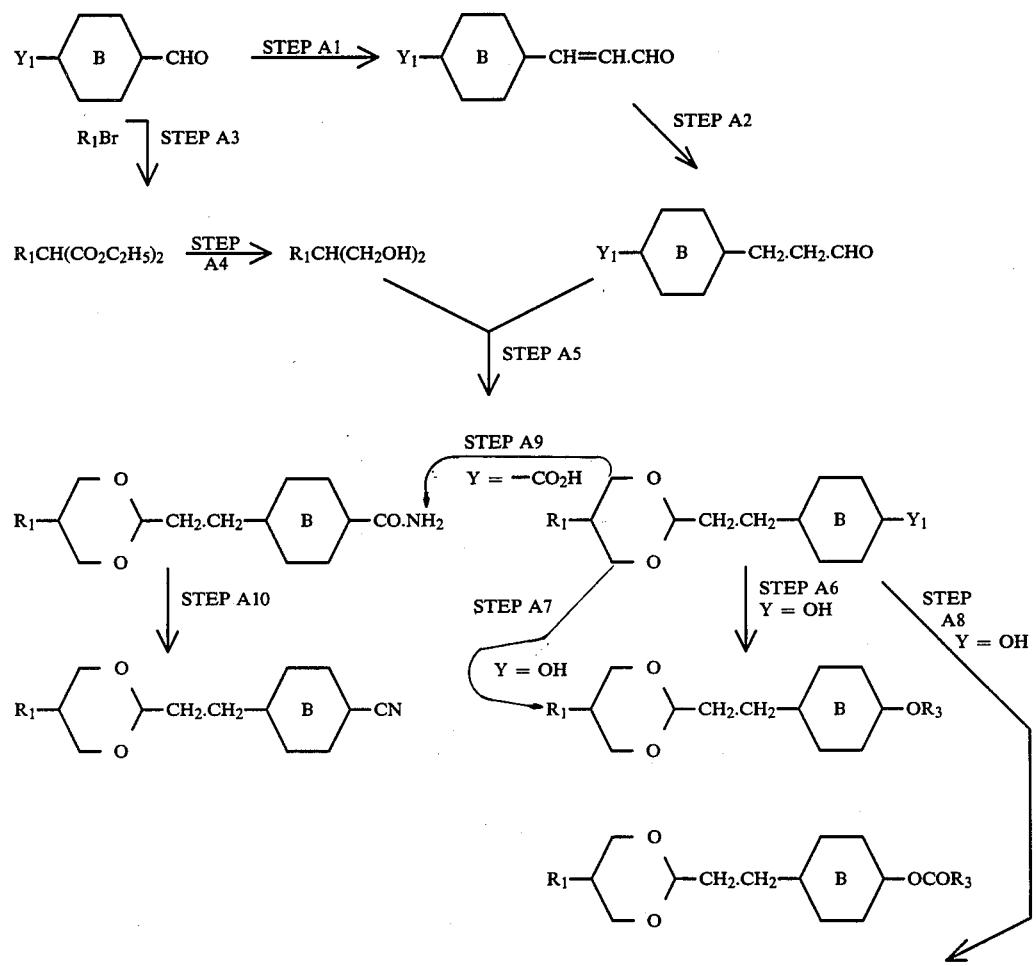

-continued
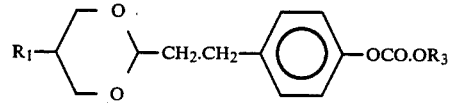
10
Compounds of Formula I wherein
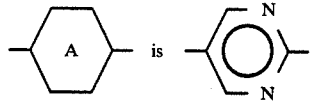 is 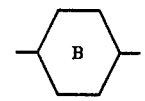
may be made by the following route, Route B:
Route B: (where $Y_2=H$, $R_3$, —OH, F or Cl and where $R_1$, $R_3$ and
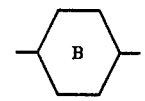
are as defined above):
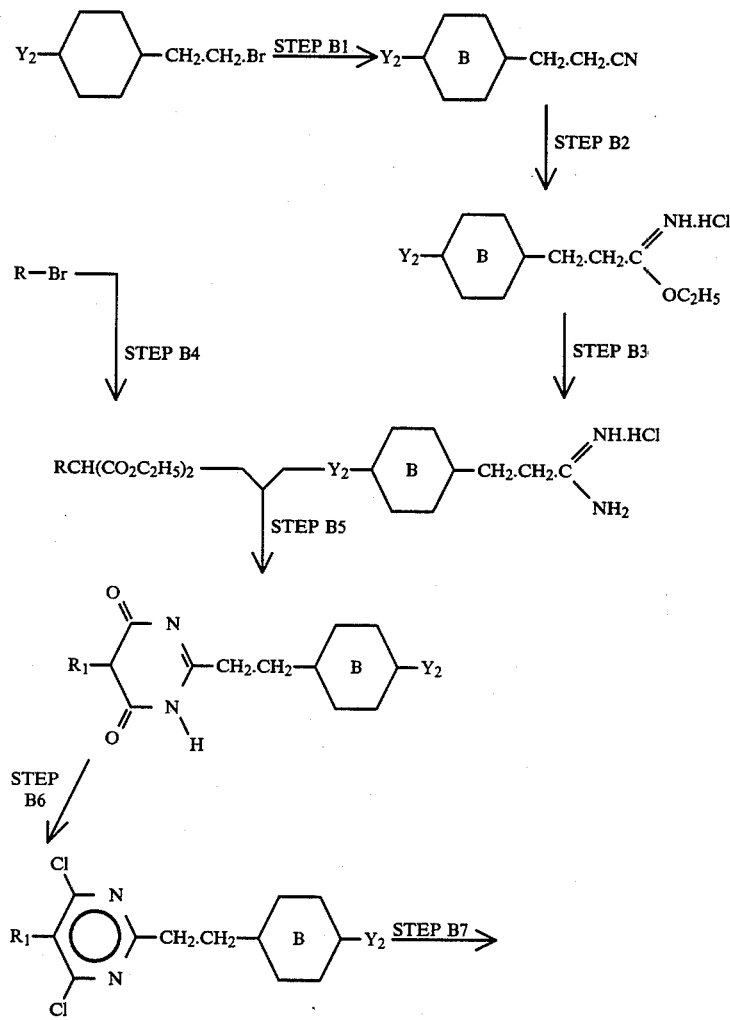

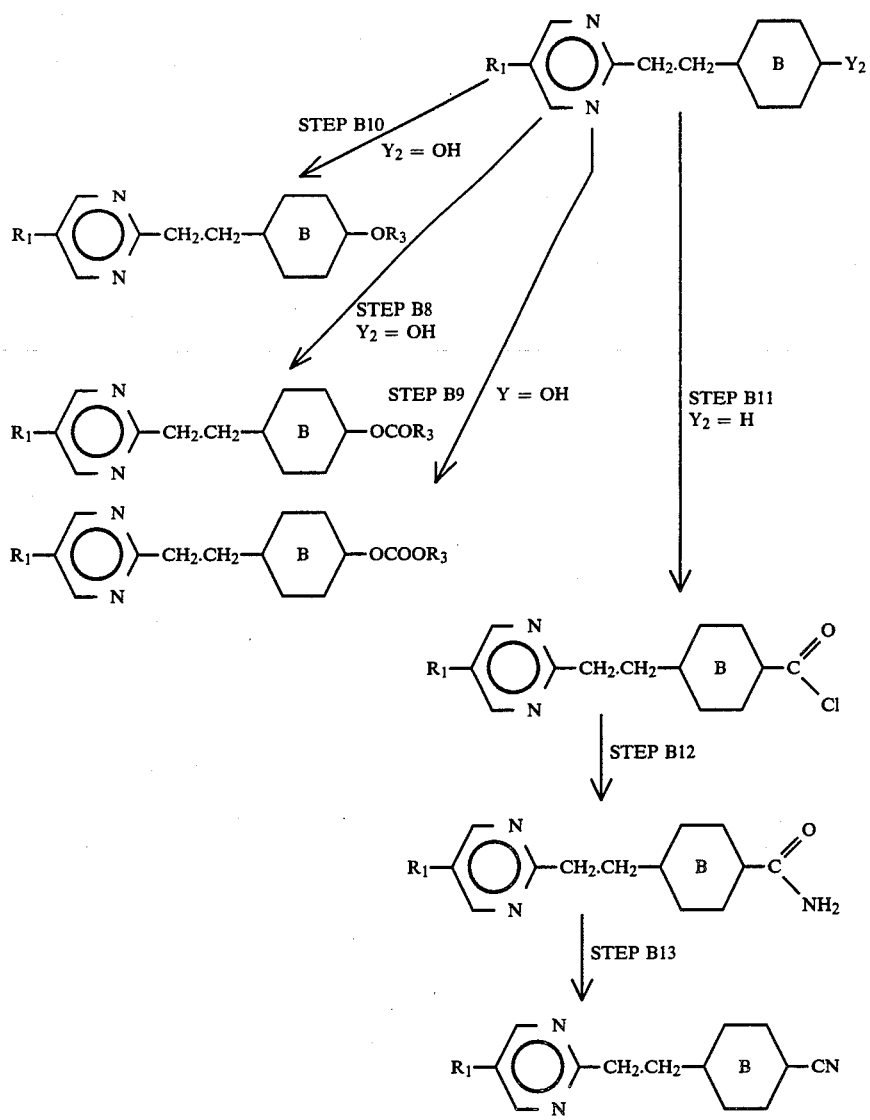

Examples of the preparation of compounds by Route A and Route B will now be given.

METHOD EXAMPLE 1

In Route A specified above Steps A1 to A10 may be carried out as follows.

STEP A1: The production of 4-substituted cinnamaldehydes from the appropriate 4-substituted benzaldehyde.

A solution of acetaldehyde (3.2 g, 0.073 mole) in absolute alcohol (30 cm³) is added to a stirred mixture of the 4-substituted-benzaldehyde (0.073 mole) in absolute alcohol (100 cm³) and aqueous 10% sodium hydroxide (20 cm³) at such a rate that the temperature is kept between 20° C. and 25° C. The reaction mixture is stirred at this temperature for 2 hours and then acidified with glacial acetic acid. The solvent is removed in vacuo and the residue is taken up in ether (80 cm³) and washed with water (5×40 cm³), dried ($Na_2So_4$), filtered and the solvent removed in vacuo. The crude 4-substituted-cinnamaldehyde is purified by column chromatography, distillation and crystallisation as appropriate.

STEP A2: The production of 3-(4'-substituted-phenyl)propionaldehydes from the corresponding 4-substituted-cinnamaldehyde produced in Step A1.

A solution of the 4-substituted-cinnamaldehyde (0.15 mole) in absolute alcohol (100 cm³) is hydrogenated at room temperature for 24 hours using palladium on carbon (1 g of 7.5%) as a catalyst. The catalyst is removed by filtration and the solvent removed in vacuo. The product is purified by distillation and crystallisation as appropriate.

STEP A3: The production of diethyl n-alkylmalonates from the appropriate n-alkyl bromide.

This Step may be carried out using a standard literature method for the alkylation of diethyl malonate using the appropriate alkyl halide (particularly the alkyl bromide)—see for example Textbook of Practical Organic Chemistry, A. I. Vogel, 4th Edition, 491 (1978).

STEP A4: The production of 2-n-alkylpropan-1,3-diols from the corresponding diethyl n-alkylmalonate produced in Step A3.

This Step may be carried out using a standard literature method for the reduction of a diester to a diol—see for example Testbook of Practical Organic Chemistry, A. I. Vogel, 4th Edition, 362 (1978).

STEP A5 The production of 1-(5'-n-alkyl-1'-3'-dioxan-2'-yl)-2-(4"-substituted-phenyl)ethanes from the appropriate 2-n-alkylpropan-1,3-diol and 3-(4'-substituted-phenyl)propionaldehyde.

A mixture of the 2-n-alkylpropan-1,3-diol (0.007 mole), produced in Step A4 and the 3-(4'-substituted-phenyl)propionaldehyde (0.007 mole) produced in Step A2 together with toluene-4-sulphonic acid (30 mg) is heated under reflux for 2½ hr in dry benzene (34 cm³) using a Dean and Stark apparatus to eliminate the water produced during the course of the reaction. The solvent is removed in vacuo and the residue taken up in ether (80 cm³); the extract is washed with aqueous 2% sodium bicarbonate (3×40 cm³), water (2×40 cm³), dried (Na₂SO₄) and, filtered, and the solvent removed in vacuo. The product is distilled whenever possible and then crystallised to yield the trans-product (the cis-product remaining in the mother liquors).

STEP A6 The production of 1-(5'-n-alkyl-1'-3'-dioxan-2'-yl)-2-(4"-n-alkoxyphenyl)ethanes from the corresponding 1-(5'-n-alkyl-1'-3'-dioxan-2'-yl)-2(4"-hydroxyphenyl)ethane produced in one example of Step A5 (where $Y_1$=OH).

This Step may be carried out using a standard literature method for the alkylation of a phenol—as for example described in the article by D. Coates and G. W. Gray in *J. Chem. Soc., Perkin II*, 867 (1976).

STEPS A7 and A8 The production of ester compounds having the formulae:

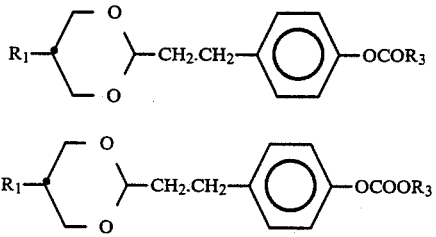

from the corresponding hydroxy compound produced in one Example of Step A5 (where $Y_1$=OH).

These Steps may be carried out in a similar way using a standard literature method for the preparation of esters from the appropriate acid chloride or alkyl chloroformate respectively and the appropriate phenol—in this case the product

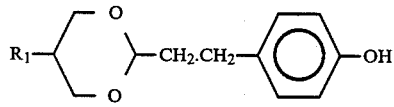

produced by Step A5. For example the method described in the article by G. W. Gray and D. G. McDonnell in *Mol. Cryst. Liq. Cryst.*, 53, 162 (1979) may be used.

STEP A9 The production of 1-(5'-n-alkyl-1'-3'-dioxan-2'-yl)-2-(phenyl-4"-carboxylic acid amide)ethanes from the corresponding 1-(5'-n-alkyl-1'3'-dioxan-2'-yl)-2-(phenyl-4"-carboxylic acid)ethane produced in one example of Step A5 (where $Y_1$=CO₂H).

This Step may be carried out by an acid to acid amide conversion essentially the same as that disclosed in published UK Patent Application No. GB 2063 288A (see in particular page 3).

STEP A10 The production of 1-(5'-n-alkyl-1'-3'-dioxan-2'-yl)-2-(4"-cyanophenyl)ethanes from the corresponding 1-(5'-n-alkyl-1'-3'-dioxan-2'-yl)-2-(phenyl-4"-carboxylic acid amide)ethane.

This dehydration Step may be carried out in essentially the same way as one of the amide dehydrations disclosed in published UK Patent Application No. GB 2063 288A (page 3) eg using benzenesulphonyl chloride in the presence of a base such as pyridine.

The pure trans-isomer of the product may be obtained from a mixture of the cis and trans isomers as described in Example 1 (page 14) of UK Patent Application No. GB 2063 288A (page 3) eg using benzenesulphonyl chloride in the presence of a base such as pyridine. The pure trans-isomer of the product may be obtained from a mixture of the cis and trans-isomers as described in Example 1 (page 14) of UK Patent Application No. GB 2063 288A.

METHOD EXAMPLE 2

In Route B above Steps B1 to B13 may be carried out as follows.

STEP B1 The production of 1-(4'-substituted phenyl)-2-cyano ethanes from the appropriate 1-(4'-substituted-phenyl)-2-bromoethane.

Sodium cyanide (28 g, 0.57 mole) in dimethyl sulphoxide (400 cm³) is heated to 150° C. until dissolved. Then a solution of the 1-(4'-substituted phenyl)-2-bromoethane (0.54 mole) in dimethyl sulphoxide (100 cm³) is added dropwise so that the temperature of the exothermic reaction does not rise above 150° C. The cooled mixture is poured into ice-water (250 cm³) and the organic material is extracted into ether (3×80 cm³). The ethereal extracts are washed with brine (3×60 cm³), dried (MgSO₄), filtered and the solvent is removed in vacuo. The crude 1-(4'-substituted phenyl)-2-cyanoethane is purified by distillation under reduced pressure.

Examples of products of this Step are:
(i) where $Y_2$=H the product has a boiling point of 75° C. at 0.1 mm Hg;
(ii) where $Y_2$=OCH₃ the product has a boiling point of 90° C. at 0.05 mm Hg.

STEP B2 The production of 3-(4'-substituted-phenyl)-1-ethoxypropyl-1-imine hydrochlorides from the corresponding 1-(4'-substituted phenyl)-2-cyanoethane produced in Step B1. The 1-(4'-substituted phenyl)-2-cyanoethane (0.27 mole) is added to ethanol (12.5 g, 0.27 mole) and the mixture is cooled to 0° C. Dry hydrogen chloride is bubbled through the mixture for 4 hr and then the mixture is left at room temperature for one hour. The precipitate is then filtered off, washed with ether and dried.

An example of the product of this Step is:
$Y_2$=H: melting point=120° C.

STEP B3 The production of 3-(4'-substituted-phenyl)propyl-1-amidine hydrochlorides from the corresponding 3-(4'-substituted-phenyl)-1-ethoxypropyl-1-imine hydrochloride produced Step B2.

The 3-(4'-substituted-phenyl)-1-ethoxypropyl-1-imine hydrochloride (0.15 mole) is dissolved in anhydrous methanol (70 cm³) and approximately 4.M methanolic ammonia (40 cm³) is added over 15 min. After addition of water (150 cm³), the solution is acidified with concentrated hydrochloric acid and the solution is washed with ether (3×60 cm³). The water is then removed in vacuo to give a white solid.

Examples of the product of this Step are:
(i) $Y_2$=H: melting point=166° C.
(ii) $Y_2$=OCH₃: melting point=150° C.

STEP B4 The production of diethyl n-alkyl malonates from the appropriate n-alkyl bromide.

This Step is carried out using a standard literature method for the alkylation of diethyl malonate using the appropriate alkylhalide (particularly the alkyl bromide)—see for example Textbook of Practical Organic Chemistry, A. I. Vogel, 4th Edition, Page 491 (1978). Product examples are:

(i) where $R_1 = n-C_3H_7$: boiling point = 70° C. at 0.2 mm Hg.

(ii) where $R_1 = n-C_5H_{11}$: boiling point = 80° C. at 0.2 mm Hg.

STEP B5 The production of 1-(5'-n-alkyl-4',6'-dihydroxy pyrimidin-2'-yl)-2-(4"-substituted phenyl)ethanes from the appropriate diethyl n-alkylmalonate produced in Step B4 and the appropriate 3-(4'-substituted-phenyl)propyl-1-amidine hydrochloride produced in Step B3.

This Step may be carried out using a standard literature method for the preparation of 5-alkyl-4,6-dihydroxy pyrimidines from the appropriate diethyl n-alkyl-malonate and the appropriate amidine hydrochloride—as described for example in the article by Arthur W. Dox and Lester Yoder in J. Amer. Chem. Soc., 44, 361(1922).

The products have melting points above 200° C.

STEP B6 The production of 1-(5'-n-alkyl-4',6'-dichloropyrimidin-2'-yl)-2-(4"substituted-phenyl)ethanes from the corresponding 1-(5'-n-alkyl-4',6'-dihydroxypyrimidin-2-yl)-2-(4"-substituted-phenyl)ethanes produced in Step B5.

This Step is carried out using a standard literature method for the chlorination of hydroxy pyrimidines as for example described in the article by A. R. Todd and F. Bergel in J. Chem. Soc., 364 (1937).

Examples of the product of Step B6 are:

(i) $R_1 = n-C_3H_7$, $Y_2 = H$: melting point = 55° C.

(ii) $R_1 = n-C_5H_{11}$, $Y_2 = H$: boiling point = 54° C. at 0.05 mm Hg.

(iii) $R_1 = n-C_5H_{11}$, $Y_2 = OCH_3$ melting point = 40° C.

STEP B7 The production of 1-(5'-n-alkylpyrimidin-2'-yl)-2-(4"-substituted-phenyl)ethanes from the corresponding 1-(5'-n-alkyl-4',6'-dichloropyrimidin-2'-yl)-2-(4"-substituted-phenyl)ethane produced in Step B6.

This Step is carried out using a standard literature method for the catalytic dehalogenation of halogenopyrimidines—as for example described in the article by A. Boller, M. Cereghetti, M. Schadt, and H. Scherrer in Mol. Cryst. Liq. Cryst. 42, 215 (1977).

Examples of the product of this Step are:

(i) $R_1 = n-C_3H_7$ $Y_2 = H$ melting point = 22° C.; clearing point = −85° C. (obtained by extrapolation) from measurements in admixture in the Material E7 obtained from BDH Chemicals Ltd, Poole, England. Viscosity (isotropic) = 13.3 cP at 20° C.

(ii) $R_1 = n-C_5H_{11}$ $Y_2 = OH$ melting point = 105° C.

STEPS B8 and B9 The production of compounds having the formula

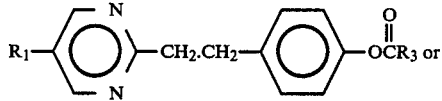

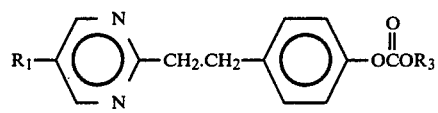

from the corresponding hydroxy compound produced in one example of Step B7, ie where $Y_2 = OH$.

This Step is carried out using a standard literature method for the preparation of esters from the appropriate acid chloride and the appropriate phenol (Step B8) or the appropriate alkyl chloroformate and the appropriate phenol, (Step B9)—as for example described in the article by G. W. Gray and D. G. McDonnell in Mol. Cryst. Liq. Cryst. 53, 162 (1979).

STEP B10 The production of 1-(5'-n-alkylpyrimidin-2'-yl)-2-(4"-n-alkoxyphenyl)ethanes from the corresponding 1-(5'-n-alkylpyrimidin-2'-yl)-2-(4"-hydroxyphenyl)ethane produced in Step B7, where $Y_2 = OH$.

This Step is carried out using a standard literature method for the alkylation of a phenol,—as for example described in the article by D. Coates and G. W. Gray in J. Chem. Soc., Perkin II, 867 (1976).

Examples of the product of Step B10 are:

(i) $R_1 = n-C_5H_{11}$, $R_3 = CH_3$: melting point = 26° C. clearing point = −15° C. (measured in the material ZLI 1132 obtained from E. Merck Co. Darmstadt, W. Germany).

(ii) $R_1 = n-C_5H_{11}$ $R_3 = C_2H_5$: melting point = 52° C. clearing point = −1.5° C.

(iii) $R_1 = n-C_5H_{11}$, $R_3 = n-C_4H_9$: melting point = 40° C.; clearing point = 4° C.

(iv) $R_1 = n-C_5H_{11}$, $R_3 = n-C_6H_{13}$: melting point = 45° C., clearing point = 10° C.

STEP B11 The production of 1-(5'-n-alkylpyrimidin-2'-yl)-2-(phenyl-4"-carboxylic acid chloride)ethanes from the corresponding 1-(5'-n-alkylpyrimidin-2'-yl)-2-phenylethane produced in one example of Step B7, where $Y_2 = H$.

This Step is carried out using a standard literature method for the production of a benzoyl chloride by Friedel-Crafts acylation of the corresponding substituted benzene with oxalyl chloride and aluminium chloride, as for example in the article by Mary E. Neubert, L. T. Carlino, R. D'Sidocky and D. L. Fishel in Mol. Cryst. Liq. Cryst., 53, 101 (1979) and also in Step 9 of copending UK Patent Application No. 8206265.

STEP B12 The production of 1-(5'-n-alkylpyrimidin-2'-yl)-2-(phenyl-4"-carboxylic acid amide)ethanes from the corresponding 1-(5'-n-alkylpyrimidin-2'-yl)-2-(phenyl-4"-carboxylic acid chloride)ethane produced in Step B11.

This Step is carried out using a standard literature method for the production of a carboxylic acid amide from the appropriate carboxylic acid chloride—as for example described by A. I. Vogel in Textbook of Practical Organic Chemistry, 4th edition, 1116 (1978) and see also Step 10 of UK Patent Application No. 8206265.

Examples of the product of this Step are:

(i) $R_1 = n-C_3H_7$: melting point = 205° C.

(ii) $R_1 = n-C_5H_{11}$: melting point = 183° C.

STEP B13 The production of 1-(5'-n-alkylpyrimidin-2'-yl)-2-(4"-cyanophenyl)ethanes from the appropriate 1-(5'-n-alkylpyrimidin-2'-yl)-2-(phenyl-4"-carboxylic acid amide)ethane produced in Step B12.

This Step is carried out using a standard literature method for the production of aromatic cyanides by the dehydration of the appropriate aromatic amide—as described for example by A. I. Vogel, Textbook of Practical Organic Chemistry, 4th edition, 1116 (1978) and also in Step 11 of UK Patent Application No. 8206265.

Examples of the product of this Step are as follows:
(i) $R_1$=n-$C_3H_7$: melting point=71° C.; clearing point=−32° C. measured in E7.
(ii) $R_1$=n-$C_5H_{11}$: melting point=51° C.; clearing point=−11° C. measured in E7; viscosity (nematic phase extrapolated)=58 cP at 20° C. measured in ZLI 1132.

Examples of compounds of the formula

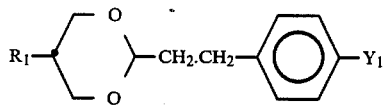

which may be made by Route A (Steps A1 to A5) are listed in Table 1 as follows together with compounds of the formula

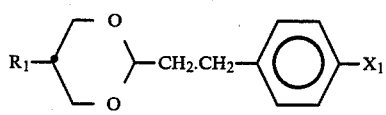

where $X_1$=$OR_3$ which may be made by Route A (Steps A1 to A5 and A6) and compounds of the formula

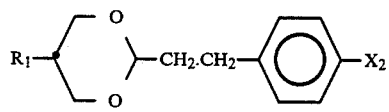

where $X_2$ is CN, which may be made also by Route A (Steps A1 to A5 and Steps A9 to A10): (one terminal substituent $Y_1X_1$ or $X_2$ of the alternative terminal substituents listed in Table 1 applying in the case of each compound).

TABLE 1
COMPOUNDS OF FORMULA

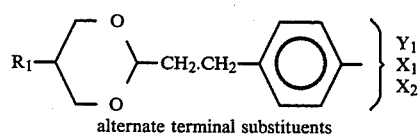

alternate terminal substituents

| $R_1$ | $Y_1$ | $Y_1$ | $Y_1$ | $Y_1$ | $X_2$ | $X_1$ |
|---|---|---|---|---|---|---|
| $CH_3$ | H | F | Cl | $R_3$ | CN | $OR_3$ |
| $C_2H_5$ | H | F | Cl | $R_3$ | CN | $OR_3$ |
| n-$C_3H_7$ | H | F | Cl | $R_3$ | CN | $OR_3$ |
| n-$C_4H_9$ | H | F | Cl | $R_3$ | CN | $OR_3$ |
| n-$C_5H_{11}$ | H | F | Cl | $R_3$ | CN | $OR_3$ |
| n-$C_6H_{13}$ | H | F | Cl | $R_3$ | CN | $OR_3$ |
| n-$C_7H_{15}$ | H | F | Cl | $R_3$ | CN | $OR_3$ |
| n-$C_8H_{17}$ | H | F | Cl | $R_3$ | CN | $OR_3$ |
| n-$C_9H_{19}$ | H | F | Cl | $R_3$ | CN | $OR_3$ |
| n-$C_{10}H_{21}$ | H | F | Cl | $R_3$ | CN | $OR_3$ |
| n-$C_{11}H_{23}$ | H | F | Cl | $R_3$ | CN | $OR_3$ |
| n-$C_{12}H_{25}$ | H | F | Cl | $R_3$ | CN | $OR_3$ |
| 2-methylbutyl | H | F | Cl | $R_3$ | CN | $OR_3$ | where $R_3$ is $CH_3$, $C_2H_5$, n-$C_3H_7$, n-$C_4H_9$, n-$C_5H_{11}$, n-$C_6H_{13}$, n-$C_7H_{15}$ n-$C_8H_{17}$, n-$C_9H_{19}$, n-$C_{10}H_{21}$, n-$C_{11}H_{23}$, n-$C_{12}H_{25}$ or 2-methylbutyl.

Examples of compounds of the formula

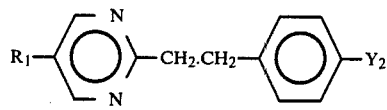

which may be made by Route B (Steps B1 to B7), and also of compounds of the formula

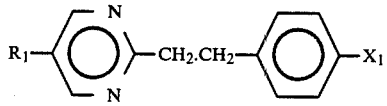

where $X_2$=$OR_3$ which may be made by Route B (Steps B1 to B7 and Step B10) and also compounds of the formula

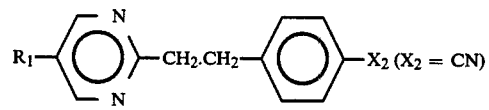

which may be made by Route B (Steps B1 to B7 and B11 to B13), are listed in Table 2 as follows: (one terminal substituent $Y_1X_1$ or $X_2$ of the alternative terminal substituents listed in Table 1 applying in the case of each compound.)

TABLE 1
COMPOUNDS OF FORMULA alternate terminal substituents

| $R_1$ | $Y_1$ | $Y_1$ | $Y_1$ | $Y_1$ | $X_2$ | $X_1$ |
|---|---|---|---|---|---|---|
| $CH_3$ | H | F | Cl | $R_3$ | CN | $OR_3$ |
| $C_2H_5$ | H | F | Cl | $R_3$ | CN | $OR_3$ |
| n-$C_3H_7$ | H | F | Cl | $R_3$ | CN | $OR_3$ |
| n-$C_4H_9$ | H | F | Cl | $R_3$ | CN | $OR_3$ |
| n-$C_5H_{11}$ | H | F | Cl | $R_3$ | CN | $OR_3$ |
| n-$C_6H_{13}$ | H | F | Cl | $R_3$ | CN | $OR_3$ |
| n-$C_7H_{15}$ | H | F | Cl | $R_3$ | CN | $OR_3$ |
| n-$C_8H_{17}$ | H | F | Cl | $R_3$ | CN | $OR_3$ |
| n-$C_9H_{19}$ | H | F | Cl | $R_3$ | CN | $OR_3$ |
| n-$C_{10}H_{21}$ | H | F | Cl | $R_3$ | CN | $OR_3$ |
| n-$C_{11}H_{23}$ | H | F | Cl | $R_3$ | CN | $OR_3$ |
| n-$C_{12}H_{25}$ | H | F | Cl | $R_3$ | CN | $OR_3$ |
| 2-methylbutyl | H | F | Cl | $R_3$ | CN | $OR_3$ | where $R_3$ is $CH_3$, $C_2H_5$, n-$C_3H_7$, n-$C_4H_9$, n-$C_5H_{11}$, n-$C_6H_{13}$, n-$C_7H_{15}$ n-$C_8H_{17}$, n-$C_9H_{19}$, n-$C_{10}H_{21}$, n-$C_{11}H_{23}$, n-$C_{12}H_{25}$ or 2-methylbutyl.

Examples of compositions incorporating compounds of Formula I and of devices containing such compositions will now be described by way of example only with reference to the accompanying drawings wherein:

FIG. 1 is a sectional view of a twisted nematic digital display;

FIG. 2 is a sectional view of the display shown in FIG. 1;

FIG. 3 shows a rear electrode configuration for FIG. 1;

FIG. 4 shows a front electrode configuration for FIG. 1;

Figure 5:
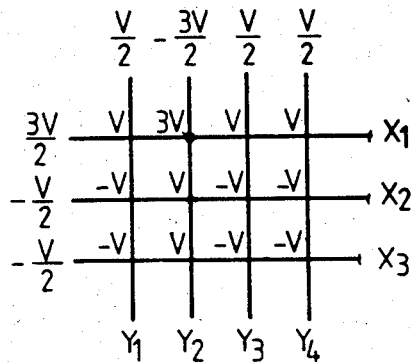
FIGS. 5, 6, 7 show schematic views of the device of FIGS. 1 to 4 with typical addressing voltages.

The display of FIGS. 1 to 4 comprises a cell 1, formed of two, front and back, glass slides 2, 3 respectively, spaced about 7 μm apart by a spacer 4 all held together by an epoxy resin glue. A liquid crystal material 12 fills the gap between the slides 2, 3 and the spacer 4. In front of the front glass slide 2 is a front polariser 5 arranged with its axis of polarisation axis horizontal. A reflector 7 is arranged behind the slide 3. A rear polariser 6 or analyser is arranged between the slide 3 and reflector 7.

Electrodes 8, 9 of tin oxide typically 100 Å thick are deposited on the inner faces of the slides 2, 3 as a complete layer and etched to the shapes shown in FIGS. 3, 4. The display has seven bars per digit 10 plus a decimal point 11 between each digit. As shown in FIG. 3 the rear electrode structure is formed into three electrodes $x_1$, $x_2$, $x_3$. Similarly the front electrode structure is formed into three electrodes per digit and decimal point $y_1$, $y_2$, $y_3$.... Examination of the six electrodes per digit shows that each of the eight elements can independently have a voltage applied thereto by application of suitable voltage to appropriate x, y electrodes.

Prior to assembly the slides 2, 3 bearing the electrodes are cleaned then dipped in a solution of 0.2% by weight of polyvinyl alcohol (PVA) in water. When dry, the slides are rubbed in a single direction with a soft tissue then assembled with the rubbing directions orthogonal to one another and parallel to the optical axis of the respective adjacent polarisers, ie so that the polarisers are crossed. When the nematic liquid crystal material 12 is introduced between the slides 2, 3 the molecules at the slide surfaces lie along the respective rubbing directions with a progressive twist between the slides.

When zero voltage is applied to the cell 1 light passes through the front polariser 5, through the cell 1 (whilst having its plane of polarisation rotated 90°), through its rear polariser 6 to the reflector 7 where it is reflected back again to an observer (shown in FIG. 1 at an angle of 45° to the axis Z normal to axes X and Y in the plane of the slides 2, 3). When a voltage above a threshold value is applied between two electrodes 8, 9 the liquid crystal layer 12 loses its optical activity, the molecules being re-arranged to lie perpendicular to the slides 2, 3 ie along the axis Z. Thus light at the position does not reach the reflector 7 and does not reflect back to the observer who sees a dark display of one or more bars of a digit 10.

Figure 6:
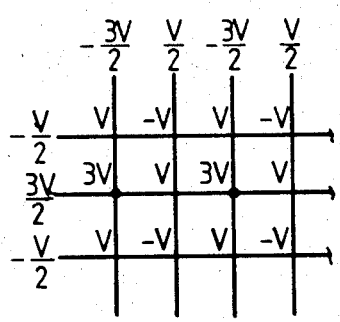
Figure 7:
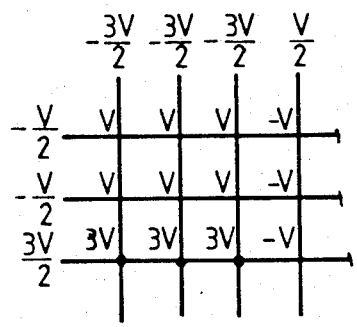

Voltages are applied as follows as shown in FIGS. 5, 6 and 7 for three successive time intervals in a linescan fashion. An electrical potential of 3 V/2 is applied to, ie scanned down, each x electrode in turn whilst $-V/2$ is applied to the remaining x electrodes. Meanwhile $-3$ V/2 or V/2 is applied to the y electrodes. A coincidence of 3 V/2 and $-3$ V/2 at an intersection results in a voltage 3 V across the liquid crystal layer 12. Elsewhere the voltage is V or $-V$. Thus by applying $-3$ V/2 to appropriate y electrodes as 3 V/2 is scanned down the x electrodes selected intersections are turned ON as indicated by solid circles. The electric voltage V is an ac signal of eg 100 Hz square wave, and the sign indicates the phase.

It will be apparent to those skilled in the art that the device shown in FIGS. 1 to 7 is a multiplexed display because the electrodes are shared between ON and OFF intersections or display elements.

A material embodying the second aspect of the invention which is suitable for use as the material 12 in the above device is in Table 3 as follows (Mixture 1).

TABLE 3

Mixture 1

| Compound | Weight percentage |
|---|---|
| $C_2H_5$—⬡—⬡—CN | 15 |
| n-$C_4H_9$—⬡—⬡—CN | 23 |
| $C_2H_5$—⟨H⟩—CO.O—⬡—⬡—CN | 12 |
| n-$C_5H_{11}$—⟨H⟩—⬡—⬡—CN | 10 |
| n-$C_3H_7$—⟨N,N⟩—$CH_2.CH_2$—⬡ | 15 |
| n-$C_5H_{11}$—⟨N,N⟩—$CH_2.CH_2$—⬡—$OC_2H_5$ | 15 |
| n-$C_3H_7$—⟨H⟩—$CH_2.CH_2$—⬡—$OC_2H_5$ | 10 |

An alternative material for use as the nematic material 12 is Mixture 2 in Table 4 as follows:

TABLE 4

Mixture 2

| Material | Weight percentage |
|---|---|
| ZLI 1289 | 70 |
| n-$C_3H_7$—⟨N,N⟩—$CH_2.CH_2$—⬡ | 30 |

ZLI 1289 is a commercially available material supplied by E Merck Co. which contains cyanobiphenyl and cyanophenylcyclohexane compounds.

Small amounts of a cholesteric material may be added to the nematic material to induce a preferred twist in the molecules in the liquid crystal layer. This and the use of appropriate slide surface treatment removes the problems of display patchiness as taught in UK Patent Ser. Nos. 1,472,247 and 1,478,592.

Suitable cholesteric materials are;

C15: about 0.1–0.5% by weight and CB15: about 0.01% to 0.05% by weight.

C15 is (+)-CH₃.CH₂.CH(CH₃).CH₂O—⬡—⬡—CN

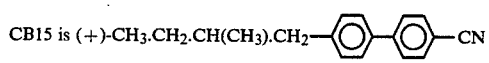
CB15 is (+)-CH₃.CH₂.CH(CH₃).CH₂—⬡—⬡—CN

Small amounts of pleochroic dye may be added to enhance the display contrast, eg one of the anthraquinone dyes described in UK Patent Specification No. 2011940A. One polariser is removed in this case.

In another embodiment mixtures embodying the second aspect of the invention may be used in a Fréedericksz effect cell. Such a cell may be constructed by sandwiching the liquid crystal material between glass slides having electrode films deposited on their inner surfaces as in the above device. However, in this case the polarisers are not necessary; the glass slide inner surfaces are treated with a coating of lecithin and the liquid crystal material is a negative material whose molecules are aligned in the OFF state perpendicular to the slide substrates (homeotropic mixture) by the lecithin coating. Application of an appropriate electric field across the material in the ON state re-arranges the molecules parallel to the slide surfaces (homogeneous texture). A pleochroic dye may be incorporated in the liquid crystal material to enhance the contrast between the ON and OFF states.

A Fréedericksz effect cell made in the above way may incorporate Mixture 3 below, the cell spacing being 10 μm.

TABLE 5
Mixture 3

| Compound | Weight percentage |
|---|---|
| 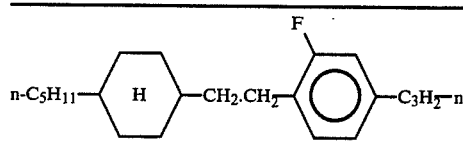 n-C₅H₁₁—⬡H—CH₂.CH₂—⬡(F)—C₃H₇-n | 30 |
| 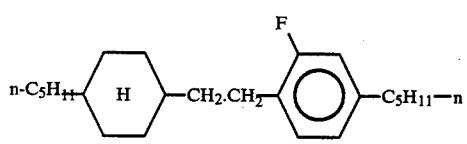 n-C₅H₁₁—⬡H—CH₂.CH₂—⬡(F)—C₅H₁₁-n | 30 |
| 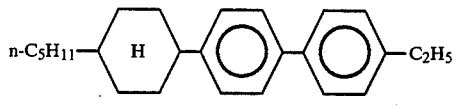 n-C₅H₁₁—⬡H—⬡—⬡—C₂H₅ | 20 |
| 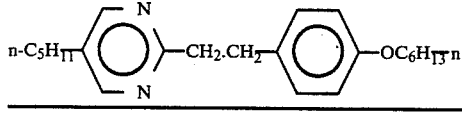 n-C₅H₁₁—⬡(N,N)—CH₂.CH₂—⬡—OC₆H₁₃n | 20 |

Compound A:
may optionally be added to Mixture 3 (up to 3% by weight of Mixture 3) as a negative additive.

The preparation of Compound A is described in published UK Patent Application No. 2061256A. About 1% by weight of a known pleochroic dye eg 1,5-bis-4'-n-butylphenylaminoanthraquinone may be added to Mixture 3 to give a dyed mixture. (Mixture 3A).

When a voltage is applied across the cell, the colour changes from a weakly absorbing state to a strongly absorbing state.

In an alternative embodiment of the invention a (cholesteric-to-nematic) phase change effect device incorporates a material as defined above.

A cell is prepared containing a long helical pitch cholesteric material sandwiched between electrode-bearing glass slides as in the twisted nematic cell described above. However the polarisers and surface preparations for homogenous alignment, eg treatment of the glass slide surfaces with SiO, are not used in this case.

If the glass slides are untreated and the liquid crystal material has a positive dielectric anisotropy (Δε) the liquid crystal material is in a twisted focal conic molecular texture in the OFF state which scatters light. The effect of an electric field applied between a pair of electrodes on the respective inner surface of the glass slides is to convert the region of liquid crystal material between the electrodes into the ON state which is a homeotropic nematic texture which is less scattering than the OFF state. This is a 'negative contrast' type of phase change effect device.

If the inner glass slide surfaces are treated, eg with a coating of lecithin, to give alignment perpendicular to those surfaces, and the liquid crystal material has Δε negative the material in the OFF state is in a homeotropic texture which has little scattering effect on incident light. If an electric field is applied between a pair of electrodes on the respective inner surfaces of the glass slides the region of liquid crystal material between the electrodes is converted to a twisted homogeneous texture which scatters light (the ON state). This is a 'positive contrast' type of phase change effect device.

The contrast between the two states in each case may be enhanced by the addition of a small amount of a suitable pleochroic dye (eg 1% by weight of 1,5-bis-4'n-butylphenylaminoanthraquinone in the case where Δε is positive) to the liquid crystal material.

A suitable positive dielectric anisotropy material, Mixture 4, embodying the invention for use in a phase change effect (negative contrast type) device is:

TABLE 6
Mixture 4

| Compound | Weight percentage |
|---|---|
| 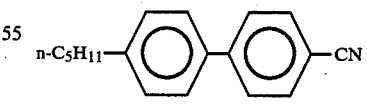 n-C₅H₁₁—⬡—⬡—CN | 25 |
| 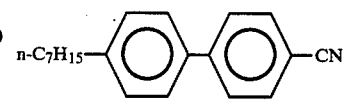 n-C₇H₁₅—⬡—⬡—CN | 25 |
| 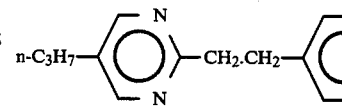 n-C₃H₇—⬡(N,N)—CH₂.CH₂—⬡—CN | 20 |

TABLE 6-continued

Mixture 4

| Compound | Weight percentage |
|---|---|
| n-C₅H₁₁—[H]—◯—◯—CN | 10 |
| CB15 = R_C—◯—◯—CN (R_C = 2-methylbutyl) | 4 |
| n-C₃H₇—[N◯N]—CH₂.CH₂—◯ | 16 |

A suitable negative dielectric anisotropy material embodying the invention for use in a phase change effect (positive contrast type) device, Mixture 5, is as follows:

TABLE 7

Mixture 5

| Material | Weight percentage |
|---|---|
| Mixture 3 | 99 |
| R_c—◯—◯—CO.O—◯—R_c (R_c = (+)-2-methylbutyl) | 1 |

An example of a high birefringence, low viscosity material of positive dielectric anisotropy suitable for simple twisted nematic displays and which includes a compound of Formula I is Mixture 6 defined in Table 8 as follows:

TABLE 8

Mixture 6

| Compound | Weight percentage |
|---|---|
| n-C₅H₁₁—◯—◯—CN | 29 |
| n-C₇H₁₅—◯—◯—CN | 17 |
| n-C₃H₇—[N◯N]—CH₂.CH₂—◯—CN | 11 |
| n-C₃H₇—[N◯N]—CH₂.CH₂—◯ | 15 |
| n-C₅H₁₁—◯—◯—◯—CN | 8 |
| n-C₅H₁₁—[H]—◯—◯—CN | 10 |
| n-C₃H₇—[H]—CO.O—◯—[H]—C₅H₁₁—n | 10 |

We claim:

1. A dioxan compound having the formula:

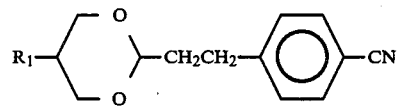

where R₁ represents an alkyl group.

2. A dioxan compound as claimed in claim 1 where $R_1$ represents an n-alkyl group having 1 to 9 carbon atoms.

3. A liquid crystal device of the type that uses a nematic liquid crystal material, including two dielectric substrates at least one of which is optically transparent, a layer of liquid crystal material sandwiched between the substrates, and electrodes on the inner surfaces of the substrates to enable an electric field to be applied across the layer of liquid crystal material to provide an electro-optic effect therein, the improvement in which the liquid crystal is a material which includes at least one compound as claimed in claim 1.

4. A liquid crystal device of the type that uses a nematic liquid crystal material, including two dielectric substrates at least one of which is optically transparent, a layer of liquid crystal material sandwiched between the substrates, and electrodes on the inner surfaces of the substrates to enable an electric field to be applied across the layer of liquid crystal material to provide an electro-optic effect therein, the improvement in which the liquid crystal is a material which includes at least one compound as claimed in claim 2.

* * * * *